(12) United States Patent
Davis

(10) Patent No.: US 9,066,578 B2
(45) Date of Patent: Jun. 30, 2015

(54) FIXED TAP LOW THRESHOLD CURRENT POWER SUPPLY

(71) Applicant: Murray W. Davis, Grosse Pointe Woods, MI (US)

(72) Inventor: Murray W. Davis, Grosse Pointe Woods, MI (US)

( * ) Notice: Subject to any disclaimer, the term of this patent is extended or adjusted under 35 U.S.C. 154(b) by 0 days.

(21) Appl. No.: 14/108,625

(22) Filed: Dec. 17, 2013

(65) Prior Publication Data

US 2014/0179174 A1 Jun. 26, 2014

Related U.S. Application Data

(60) Provisional application No. 61/740,517, filed on Dec. 21, 2012.

(51) Int. Cl.
| | |
|---|---|
| *G01R 1/20* | (2006.01) |
| *A46B 9/02* | (2006.01) |
| *H02G 1/02* | (2006.01) |
| *G01B 11/06* | (2006.01) |
| *G01W 1/14* | (2006.01) |
| *G01R 19/00* | (2006.01) |
| *G01R 31/08* | (2006.01) |
| *G01N 27/22* | (2006.01) |
| *H01F 38/30* | (2006.01) |
| *H04N 5/225* | (2006.01) |
| *G01D 11/30* | (2006.01) |
| *G01K 13/00* | (2006.01) |
| *H01F 27/02* | (2006.01) |
| *H01F 27/22* | (2006.01) |
| *H01R 4/28* | (2006.01) |
| *G01R 1/22* | (2006.01) |

(52) U.S. Cl.
CPC ........... *A46B 9/028* (2013.01); *Y10T 29/49117* (2015.01); *H02G 1/02* (2013.01); *G01B 11/0616* (2013.01); *G01W 1/14* (2013.01); *G01R 1/20* (2013.01); *G01R 19/0092* (2013.01); *G01R 31/08* (2013.01); *G01N 27/223* (2013.01); *G01R 19/0084* (2013.01); *H01F 38/30* (2013.01); *H04N 5/2252* (2013.01); *G01D 11/30* (2013.01); *G01K 13/00* (2013.01); *H01F 27/02* (2013.01); *H01F 27/22* (2013.01); *H01R 4/28* (2013.01); *A46B 2200/3073* (2013.01); *G01R 1/22* (2013.01)

(58) Field of Classification Search
None
See application file for complete search history.

(56) References Cited

U.S. PATENT DOCUMENTS

| | | | |
|---|---|---|---|
| 2,303,824 A | 12/1942 | Comins | |
| 2,306,117 A | 12/1942 | Dunlap | |
| 3,267,507 A | 8/1966 | Cox | |
| 3,622,867 A * | 11/1971 | Topper et al. | 323/341 |
| 3,861,197 A | 1/1975 | Adler | |
| 4,032,842 A | 6/1977 | Green et al. | |
| 4,052,000 A | 10/1977 | Honikman | |

(Continued)

FOREIGN PATENT DOCUMENTS

| | | |
|---|---|---|
| CN | 202041573 | 8/2009 |
| JP | 2003-061752 | 9/2004 |

*Primary Examiner* — Paresh Patel
(74) *Attorney, Agent, or Firm* — Carlson, Gaskey & Olds, P.C.

(57) ABSTRACT

A device connectable to an electric power line conductor including an electrically conductive insulated wire wound at least twice. A first end of the wire is configured to be connected to a first power line conductor and a second end of the wire is configured to be connected to a second power line conductor. A housing is mountable to the wire and includes an iron core power supply transformer configured to surround the wire to power a power supply module.

26 Claims, 10 Drawing Sheets

(56) References Cited

U.S. PATENT DOCUMENTS

| | | | |
|---|---|---|---|
| 4,061,963 A | 12/1977 | Green | |
| 4,234,863 A | 11/1980 | Shumway et al. | |
| 4,242,930 A | 1/1981 | Myers et al. | |
| 4,268,818 A | 5/1981 | Davis et al. | |
| 4,326,316 A | 4/1982 | Dolenti | |
| 4,384,289 A * | 5/1983 | Stillwell et al. | 340/870.17 |
| 4,420,752 A | 12/1983 | Davis et al. | |
| 4,546,340 A * | 10/1985 | Kuchuris | 336/192 |
| 4,728,887 A | 3/1988 | Davis | |
| 4,746,241 A | 5/1988 | Burbank | |
| 4,801,937 A | 1/1989 | Fernandes | |
| 4,806,855 A | 2/1989 | Davis | |
| 4,821,138 A * | 4/1989 | Nakano et al. | 361/93.6 |
| 4,827,272 A | 5/1989 | Davis | |
| 4,904,996 A * | 2/1990 | Fernandes | 340/870.07 |
| 5,029,101 A | 7/1991 | Fernandes | |
| 5,107,200 A * | 4/1992 | Dohnal et al. | 323/340 |
| 5,140,257 A | 8/1992 | Davis | |
| 5,232,518 A | 8/1993 | Nath et al. | |
| 5,341,088 A | 8/1994 | Davis | |
| 5,351,359 A | 10/1994 | Golden | |
| 5,426,360 A | 6/1995 | Maraio et al. | |
| 5,883,511 A * | 3/1999 | Foster | 324/174 |
| 5,966,008 A * | 10/1999 | Maier et al. | 324/96 |
| 6,151,065 A | 11/2000 | Steed et al. | |
| 6,157,160 A | 12/2000 | Okawa et al. | |
| 6,299,824 B1 | 10/2001 | Mayr et al. | |
| 6,611,189 B2 * | 8/2003 | Sigl | 336/198 |
| 6,713,670 B2 | 3/2004 | Stern et al. | |
| 6,741,069 B1 | 5/2004 | Klemar et al. | |
| 6,924,732 B2 | 8/2005 | Yokoo | |
| 6,983,508 B2 | 1/2006 | Saurer | |
| 7,030,593 B2 | 4/2006 | Pinkerton et al. | |
| 7,046,124 B2 * | 5/2006 | Cope et al. | 375/258 |
| 7,102,478 B2 * | 9/2006 | Pridmore et al. | 336/176 |
| 7,127,972 B2 | 10/2006 | Klein et al. | |
| 7,135,988 B2 * | 11/2006 | Kawai et al. | 340/870.17 |
| 7,234,669 B2 * | 6/2007 | Franks, Jr. | 248/63 |
| 7,310,109 B2 | 12/2007 | Dottling et al. | |
| 7,412,338 B2 | 8/2008 | Wynans et al. | |
| 7,432,787 B2 | 10/2008 | Muench et al. | |
| 7,545,140 B2 | 6/2009 | Humphreys et al. | |
| 7,557,563 B2 | 7/2009 | Gunn et al. | |
| 7,570,045 B2 | 8/2009 | Wolfe et al. | |
| 7,579,824 B2 | 8/2009 | Rea | |
| 7,706,596 B2 | 4/2010 | Garvey | |
| 7,932,480 B2 * | 4/2011 | Gu et al. | 219/482 |
| 8,022,291 B2 | 9/2011 | Thomsen et al. | |
| 8,144,445 B2 | 3/2012 | Caggiano et al. | |
| 8,184,015 B2 | 5/2012 | Lilien et al. | |
| 8,203,328 B2 | 6/2012 | Bose et al. | |
| 8,300,922 B1 | 10/2012 | Garvey, III | |
| 8,320,146 B2 | 11/2012 | Haines et al. | |
| 8,322,332 B2 | 12/2012 | Rogers | |
| 8,400,504 B2 | 3/2013 | Al-Duwaish et al. | |
| RE44,256 E | 6/2013 | Bright et al. | |
| 8,536,857 B2 | 9/2013 | Nero, Jr. | |
| 8,628,211 B2 | 1/2014 | Jensen et al. | |
| 8,686,302 B2 | 4/2014 | Brasher et al. | |
| 2004/0012678 A1 | 1/2004 | Li | |
| 2006/0060007 A1 | 3/2006 | Mekhanoshin | |
| 2006/0125469 A1 | 6/2006 | Hansen | |
| 2008/0077336 A1 | 3/2008 | Fernandes | |
| 2008/0136403 A1 | 6/2008 | Deck | |
| 2008/0297162 A1 | 12/2008 | Bright | |
| 2009/0207421 A1 | 8/2009 | Kelly et al. | |
| 2009/0212241 A1 | 8/2009 | Mcgeoch | |
| 2009/0243876 A1 | 10/2009 | Lilien et al. | |
| 2010/0085036 A1 | 4/2010 | Banting et al. | |
| 2010/0192975 A1 | 8/2010 | Schweikert | |
| 2011/0204879 A1 | 8/2011 | Peretto | |
| 2011/0308566 A1 | 12/2011 | Johnson | |
| 2012/0086804 A1 | 4/2012 | Ishibashi et al. | |
| 2012/0152346 A1 | 6/2012 | Yang et al. | |
| 2013/0022078 A1 | 1/2013 | Phillips et al. | |
| 2013/0179079 A1 | 7/2013 | Lancaster | |
| 2014/0110376 A1 | 4/2014 | Zahlmann et al. | |

\* cited by examiner

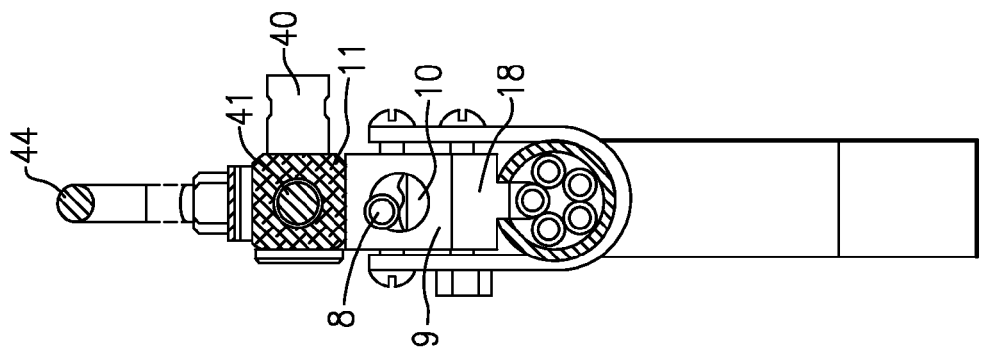
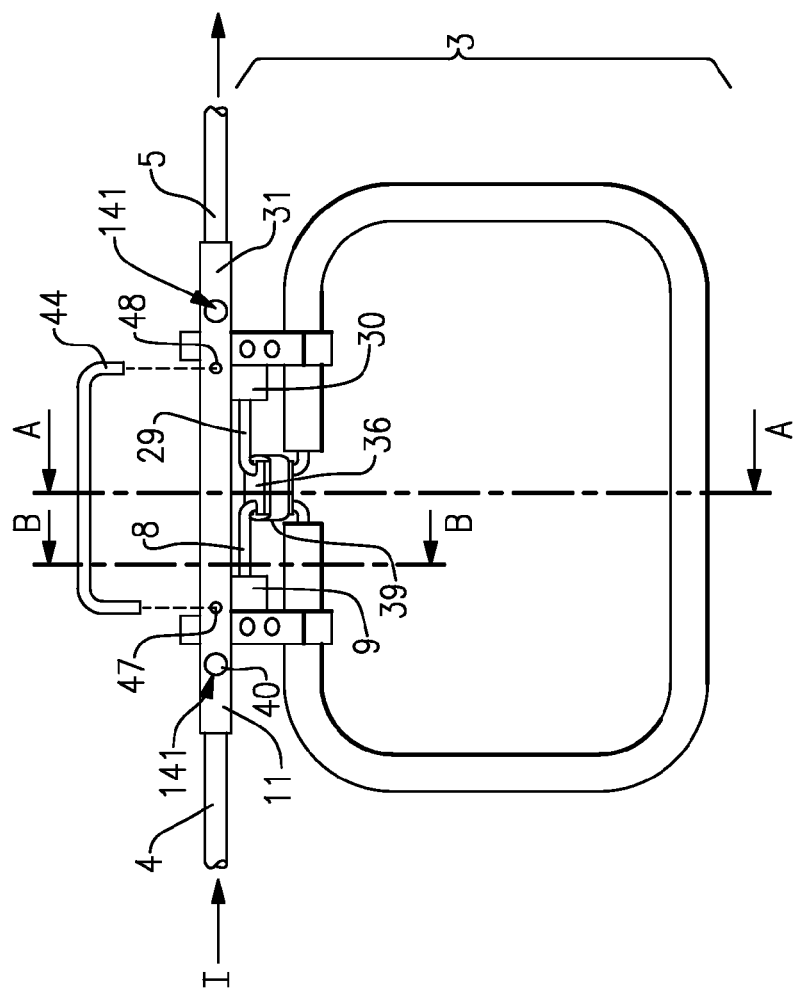

FIXED TAP LOW THRESHOLD CURRENT POWER SUPPLY

CROSS-REFERENCE TO RELATED APPLICATIONS

The application claims priority to U.S. Provisional Application No. 61/740517 which was filed on Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device which is low maintenance and can be constantly powered independent of weather conditions over a wide range of current levels in the power line.

SUMMARY

A device connectable to an electric power line conductor including an electrically conductive insulated wire wound at least twice. A first end of the wire is configured to be connected to a first power line conductor and a second end of the wire is configured to be connected to a second power line conductor. A housing is mountable to the wire and includes an iron core power supply transformer configured to surround the wire to power a power supply module.

A device connectable to an electric power line conductor including a loop tube providing a form and at least two turns of electrically conductive and insulated wire surrounding the loop tube configured to be connected in series with a first electric power line conductor and a second electric power line conductor.

These and other features of the disclosed examples can be understood from the following description and the accompanying drawings, which can be briefly described as follows.

BRIEF DESCRIPTION OF THE DRAWINGS

FIG. 2 illustrates a front view of the LTPS of FIG. 1.

FIG. 3 illustrates a cross-sectional view taken along line B-B of the LTPS of FIG. 2.

DETAILED DESCRIPTION

Figure 1:
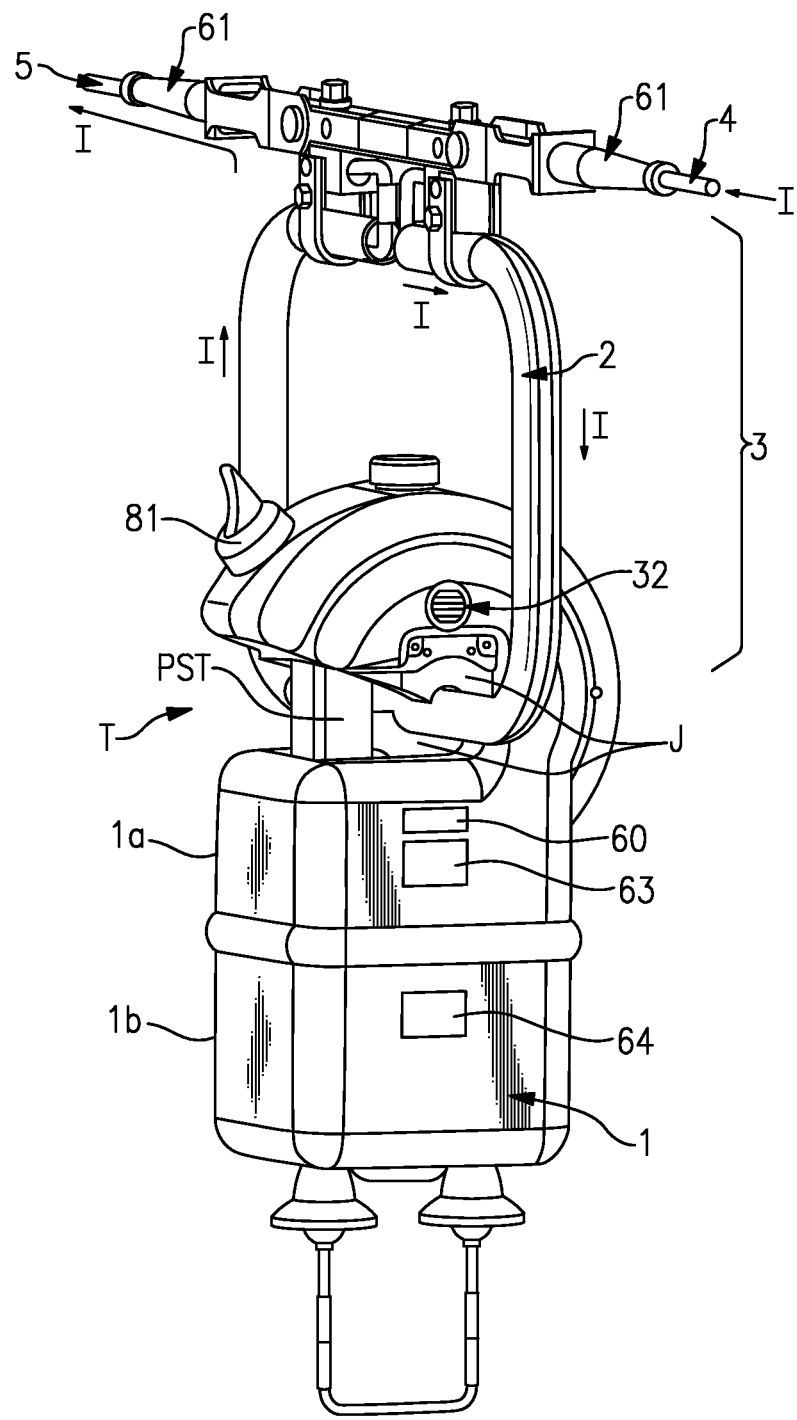
FIG. 1 illustrates an STR unit mounted on a low threshold current power supply ("LTPS").

FIG. 1 illustrates an example sensor transmitter receiver unit ("STR unit") 1 attached to a low threshold current power supply ("LTPS") 3. The STR unit 1 includes an upper housing 1a and a lower housing 1b. The upper housing 1a includes a throat T for accepting an electric power line conductors or an aluminum loop tube 2.

The STR unit 1 includes an iron core power supply transformer PST that surrounds one of the power line conductors 4 and 5 or the loop tube 2 when a pair of jaws J are clamped onto one of the power line conductors 4 and 5 or the loop tube 2.

Figures 4, 5:
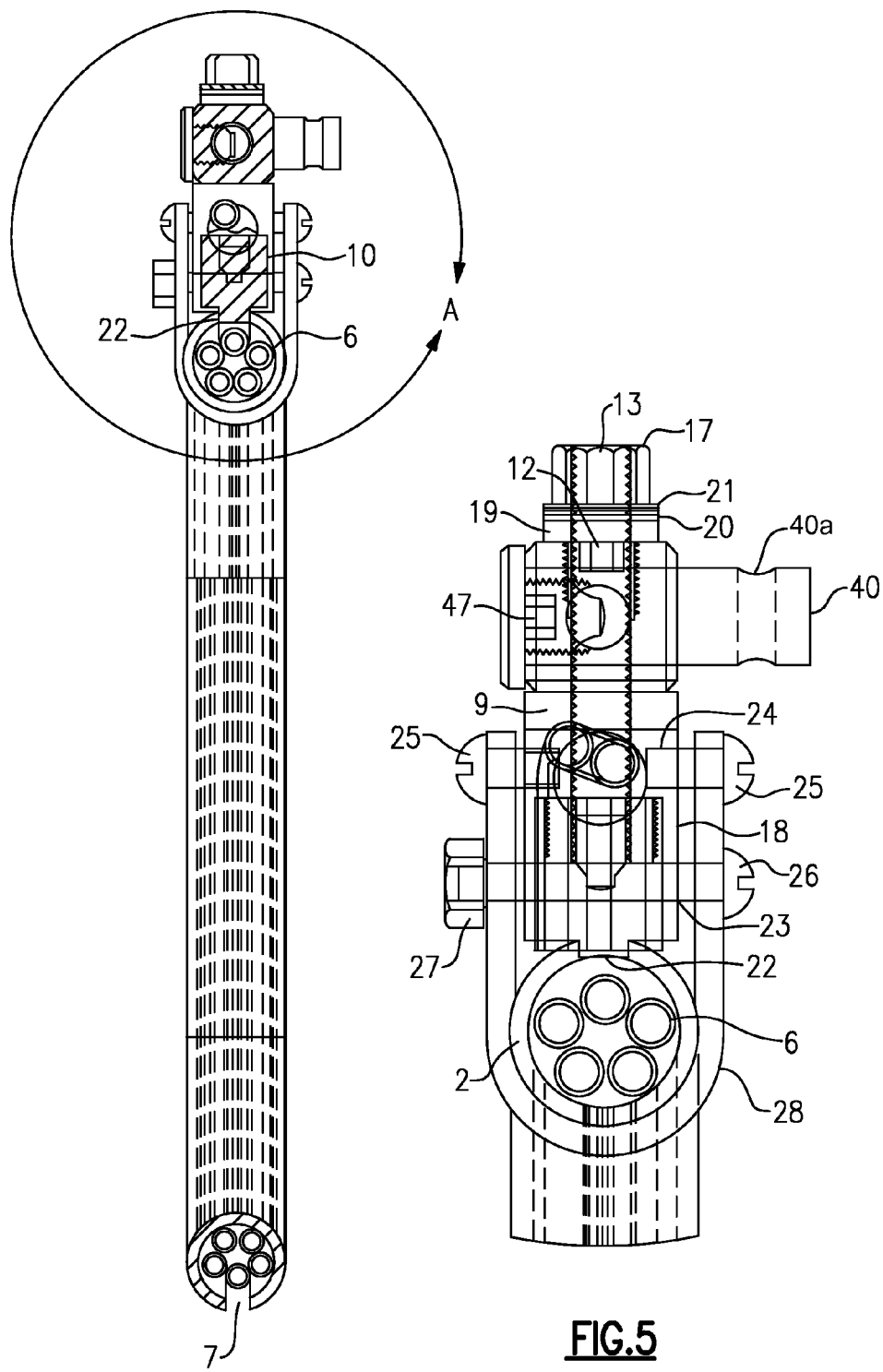
FIG. 4 illustrates a cross-sectional view taken along line A-A of FIG. 2.
FIG. 5 illustrates an enlarged detail of circle A in FIG. 4.

As shown in FIGS. 3-5, the loop tube 2 includes five turns of insulated copper wire 6 wound inside and around the loop tube 2. The wire 6 is wound inside the loop tube 2 through a slot 7 which extends around an outside perimeter of the loop tube 2. Except for the top turn of the wire 6, the four remaining turns are in intimate contact with each other and in contact with the inside wall of the loop tube 2. Since the slot 7 is located around the outside of the loop tube 2, a temperature of the winding of wire 6 will run cooler when current is flowing through 6 than if the loop tube 2 were enclosed.

The five turns of the wire 6 are in thermal contact with each other. Heat generated by the power line conductor current I flowing through the five turns or $I^2R$, R being the resistance of each turn, is conducted through a wall of the loop tube 2 and is lost by thermal convection and thermal radiation to the outside environment. Because the top turn of the wire 6 is in contact with the other 4 turns of the wire 6, the top turn of the wire 6 not only loses its heat by conduction through the wall of the loop tube 2, but also directly to the environment through the slot 7 by thermal convection and thermal radiation. The loop tube 2 not only acts as a form onto which the wire 6 is wound, but also becomes a convoluted fin to effectively transfer heat to the surrounding environment.

In one example, the low threshold power supply 3 must be capable of carrying a maximum single phase (SØ) lateral current of 200 amperes per turn without exceeding the maximum temperature limit of the insulation on the wire 6.

Figure 8:
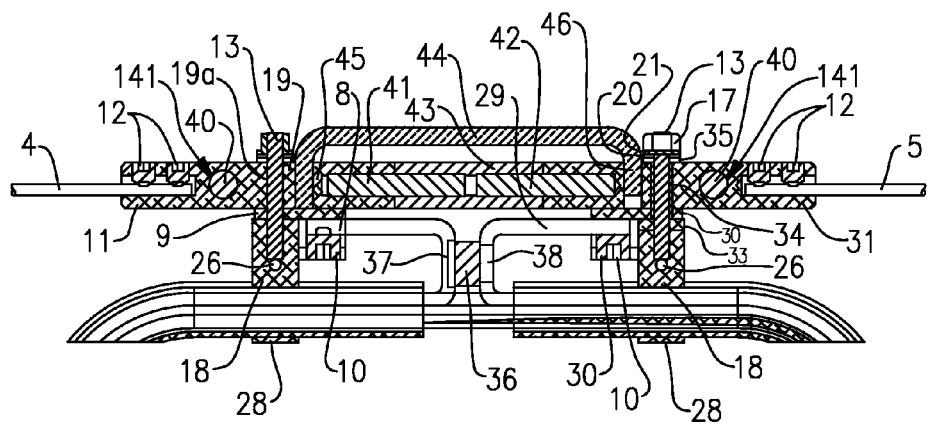
FIG. 8 illustrates a cross-sectional view taken along line C-C of FIG. 7.

FIG. 8 illustrates a beginning of a first turn 8 of wire 6 of the five turns. A beginning of the first turn 8 is connected to a left side connector 9 using a set screw 10. The connector 9 is electrically connected to a left anchor rod 11. The power line conductor 4 is electrically connected to the left anchor rod 11 using two set screws 12. The connector 9 is held securely against the left anchor rod 11 with a threaded stud 13 which fits through a vertical centered hole in the connector 9 and is screwed into a lock block 18 on one end and is inserted in the vertical hole 19a of the left anchor rod 11 on the other end.

The threaded stud 13 draws the lock block 18 up tight against the connector 9 and the left anchor rod 11 using a metal spacer washer 19, a flat washer 20, a lock washer 21, and a nut 17, as shown in FIGS. 5 and 8. The lock block 18 serves three purposes: First, the lock block 18 provides a mechanism of holding the connector 9 tight against the left anchor rod 11 using the threaded stud 13 and the nut 17. Second, the lock block 18 includes a projection 22 on a bottom end which fits into the slot 7 and prevents the loop tube 2 from rotating. Third, the lock block 18 has two sets of horizontal holes 23 and 24 (see FIG. 5) through which bolts 25 are threaded into the lock block 18 and a through bolt 26 and a nut 27 holds a band 28.

The band 28 pulls the slot 7 of the loop tube 2 up and into the projection 22 which in turn supports the loop tube 2. An electrically conductive path exists from the power line conductor 4, through the electrically conductive left anchor rod 11, the electrically conductive connector 9, and on to the beginning of the first turn 8 of the winding of wire 6. As mentioned earlier, there are five turns of the wire 6 that surround the loop tube 2. An end of a last turn 29 of the wire 6 terminates in a right connector 30, which is electrically attached to a right side anchor rod 31 and the power line conductor 5. (See FIG. 8). The power line conductor 5 is held securely to the right side anchor rod 31 with two set screws 12.

The current path inside of the loop tube 2 is counterclockwise and as such the direction of the current at the bottom of the loop tube 2 is in the same direction as the path of the current in the power line conductors 4 and 5. (See the direction arrows of current I flow in FIG. 1). When the STR unit 1 is installed on the bottom of the loop tube 2, a polarity mark 32 (see FIG. 1) of the STR unit 1 must match the direction of current I coming into the polarity mark 32. The end of the last turn 29 is inserted into the connector 30, and a set screw 10 is tightened onto an end of the conductor 29, as shown in FIG. 8.

The power line current only flows through the five windings of wire 6. None of the current is diverted through the electrically conductive loop tube 2 even though the loop tube 2 is mechanically fixed on each end using the bands 28 which are held in place by the screws 25 and through bolt 26 and nut 27 to the lock blocks 18.

Figure 7:
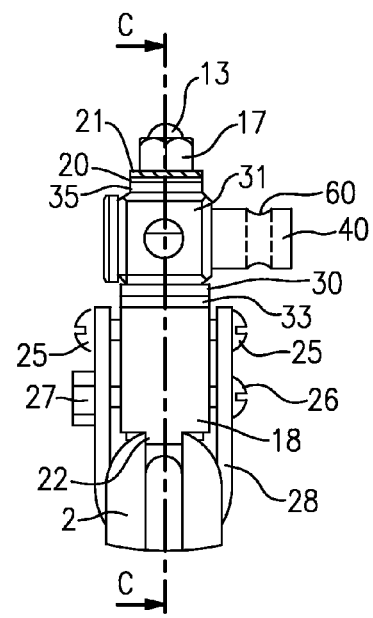
FIG. 7 illustrates an enlarged detail of circle B on the right side of FIG. 6.

In FIGS. 7 and 8, the lock block 18 and right side threaded stud 13 are electrically isolated from the connector 30 and right side anchor rod 31 using an electrically insulating square washer 33, an electrically insulating sleeve 34, and an electrically insulating washer 35. If the loop tube 2 was not electrically insulated from the winding of wire 6 and the left and right anchor rods 11 and 31, which are in turn connected to the power line conductors 4 and 5, then a portion of the power line current would by-pass the winding of wire 6 and the STR unit 1 would not receive the full amount of line current times the number of turns in the winding of wire 6.

It should be noted that the beginning of the first turn 8 and the end of last turn 29 are each bent into a horizontal "U" shape. An electrically insulating bridge 36 with vertically recessed grooves 37 and 38 on opposite sides is inserted between the two vertical portions of the "U" shaped windings. The grooves 37 and 38 include a groove diameter similar to the size of the wire 6.

Once the bridge 36 is inserted between the two vertical sections of the winding of wire 6 and the grooves 37 and 38 are fully engaged with the two vertical sections, both the bridge 36 and the winding of wire 6 are wrapped with a strong insulating tape 39 (see FIG. 2) to pull any slack out of the wire 6 and thus increase the rigidity of the winding of wire 6. The purpose of the bridge 36 and the tape 39 is to hold the turns of the winding of wire 6 tightly together and to the inside of the loop tube 2, because heavy fault currents from the power line conductors 4 and 5 of 10,000 to 20,000 amperes will create high opposing forces on the turns of the winding of wire 6. These forces can loosen the connections at the first turn 8 at the connector 9 and at the last turn 29 at the connectors 30, and damage the turns of the winding of wire 6 by pushing them apart.

The anchor rods 11 and 31, shown in FIG. 8, serve four functions: (1) To provide the same or greater line tension capability as the power line conductors 4 and 5 itself, because the power line conductors 4 and 5 are deadened mechanically on each end of the anchor rods using pins 40; (2) To provide the same or greater current carrying capacity as the power line conductors 4 and 5, because the power line conductors 4 and 5 are electrically connected to the anchor rods 11 and 31 using the two sets of set screws 12 on each end of the anchor rods 11 and 31; (3) To physically support the loop tube 2, the wire 6, and the STR unit 1 through the use of the two threaded studs 13, the lock blocks 18, and the bands 28; and (4) To provide an electrical path for current from the power line conductors 4 and 5 to the connectors 9 and 30 and the wire 6.

In viewing FIG. 8, the two anchor rods 11 and 31 are held together with a left side threaded stud 41 and a right side threaded stud 42 and an electrically insulating spacer rod 43. The left side threaded stud 41 is screwed into the left anchor rod 11 and into the spacer rod 43. The right side threaded stud 42 is threaded into the right side anchor rod 31 and the spacer rod 43. As a unit, the left and right side anchor rods 11 and 31 and the spacer rod 43 are capable of full electric power line tension.

The function of the electrically insulated spacer rod 43 is to electrically isolate the left side anchor rod 11 and power line conductor 4 from the right side anchor rod 31 and the power line conductor 5. The left and right threaded studs 41 and 42 do not touch each other inside the threaded hole of the spacer rod 43. Therefore, the spacer rod 43 prevents any power line current from flowing through this unit of the left and right anchor rods 11, and 31 so that all current flows through the wire 6.

The LTPS 3 is designed such that if it is desirable to remove the loop tube 2 and the wire 6, an electrically conducting shorting bar 44 is provided as shown in FIGS. 7 and 8. Insertion of the shorting bar 44 in holes 45 and 46 of FIG. 8 and tightening of the two set screws 47 and 48 (see FIG. 2) onto the shorting bar 44, creates an electrical "by-pass" path of power line current from the power line conductor 4 through left side anchor rod 11 to the right side anchor rod 31 through the shorting bar 44. Since the shorting bar 44 is installed before the loop tube 2 is disconnected by removing the threaded studs 13, then there is no power interruption to customers, because the load current now flows through the shorting bar 44.

The loop tube 2, the windings of wire 6, the connectors 9 and 30, and the lock blocks 18 are removed as a complete assembly by removing the two threaded studs 13. In summary, to remove a low threshold current power supply 3, install the shorting bar 44 and remove the two nuts 17 on the threaded studs 13. With the loop tube 2 removed, the left and right anchor rods 11 and 31, the shorting bar 44 and spacer rod 43 can remain indefinitely on the power line conductors 4 and 5, or until the loop tube 2 is again re-installed at this location.

As mentioned earlier the pins 40 of FIGS. 7 and 8 in the left and right anchor rods 11 and 31 are an integral part of the different installation methods for the fixed tap LTPS 3.

Although five methods will be described, these are not to be considered as the only methods of installation. One skilled in electric power utility construction may envision other variants to the installation methods outlined below.

Figure 9:
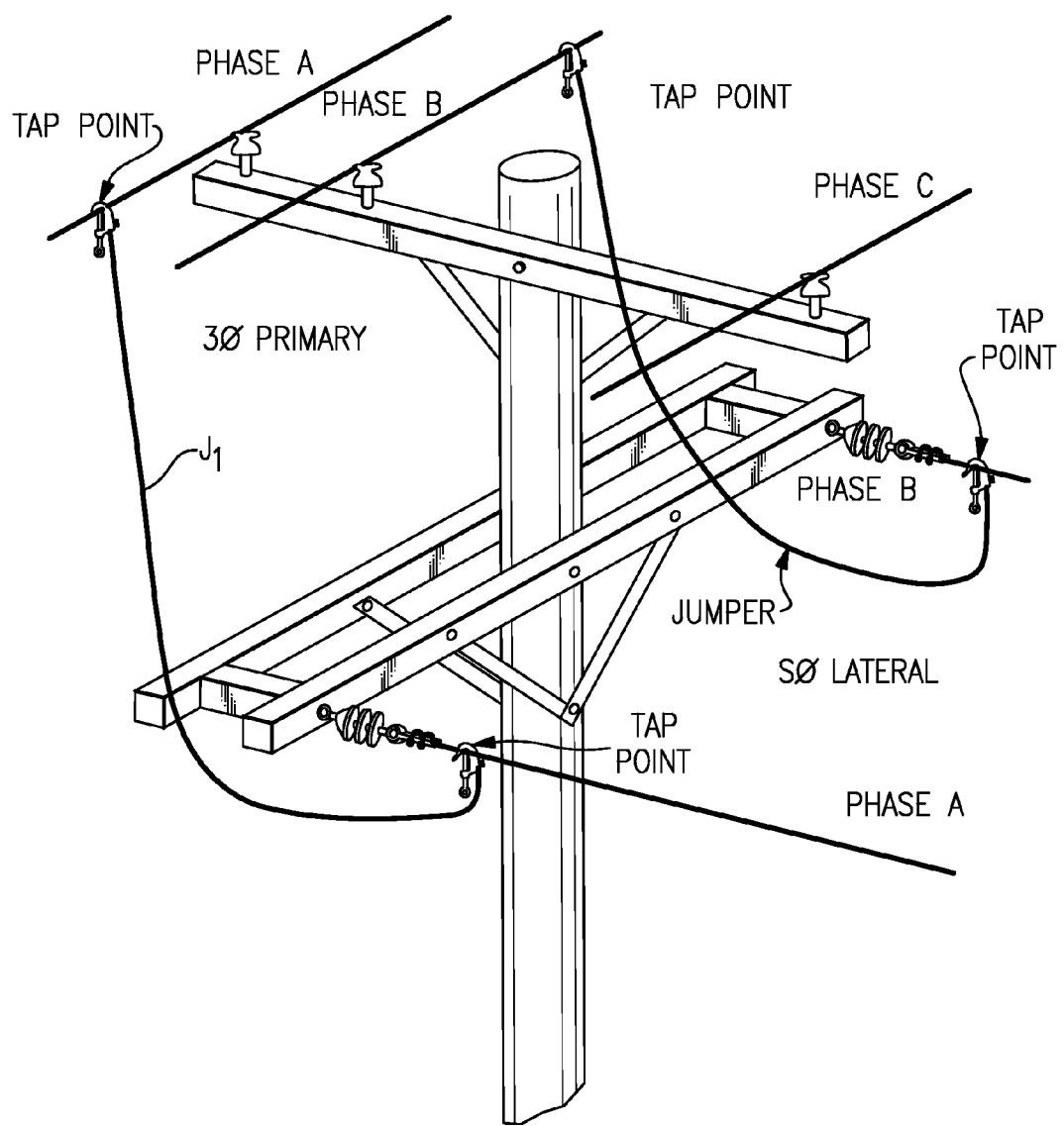
FIG. 9 illustrates tap points of a single phase lateral off of phases "A" and "B" of the three phase primary for a delta connected electric power system.

FIG. 9 illustrates a jumper J1 from the tap point on phase A of the 3∅ primary to the tap point on the phase A of the S∅ lateral. The first installation method shown in FIG. 10 bridges the jumper with the LTPS 3.

Figure 10:
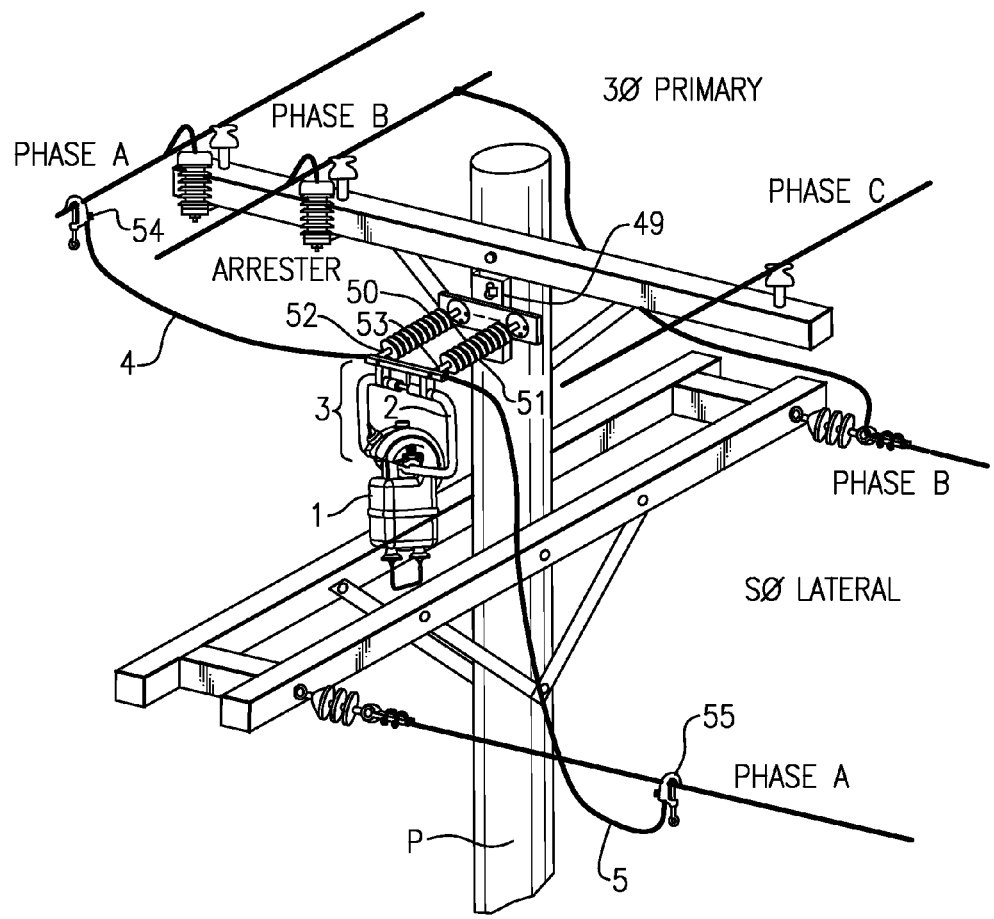
FIG. 10 illustrates the LTPS suspended from a pole mounted bracket for measuring current of phase A for the delta connected electric power system.

FIG. 10 illustrates a pole mounted cantilevered insulator method of installing the LTPS 3 for a delta connected electric power system. The installation method of FIG. 10 is especially suitable for small power line conductors (such as No. 6 AWG copper) where the weight of the STR unit 1 and LTPS 3 may cause concern for old construction where the copper conductor is fully annealed. A pole mounted bracket 49 includes two horizontal spaced apart cantilevered insulators 50 and 51, which are attached to the pole mounted bracket 49, installed at the top of the utility pole P. Two end caps 52 and 53 on the ends of the insulators 50 and 51 have the same diameter as holes 141 of FIG. 2 in the left and right anchor rods 11 and 31. The holes 141 in the left and right anchor rods 11 and 31 are spaced the same distance apart as the two cantilevered insulators 50 and 51.

The LTPS 3 is installed on the two end caps 52 and 53, which have holes drilled at the outside extremity for cotter pins. Once the LTPS 3 is in place, the cotter pins are inserted into these holes to prevent the left and right anchor rods 11 and 31 from sliding off the end caps 52 and 53. The jumper J1 of FIG. 9 remains in place with one end attached to phase A of the 3∅ primary and the other end attached to phase A of the S∅ lateral. Therefore, there is no interruption of service to customers fed off of phase A of the S∅ lateral.

Next the power line conductor 4 of the LTPS 3 of FIG. 10 is attached using a hotstick to phase A of the 3∅ primary with a hot line clamp 54 and the power line conductor 5 of the LTPS 3 is attached using a hotstick to phase A with a hot line clamp 55 to phase A of the SO lateral. The jumper J1 is then removed, and current now flows through the LTPS 3 winding of wire 6 without a service interruption. The STR unit 1 is then installed on the loop tube 2 of the LTPS 3. Once the STR unit 1 is installed on the LTPS 3, the current traveling through the winding of wires 6 generate power for the power supply transformer PST for the STR unit 1. The power generated from the power supply transformer is sent to a power supply module 60 to power an onboard electronics module 63, a transmitter/receiver 64, and an antenna 81 (see FIG. 1) and begins to transmit data.

Figure 6:
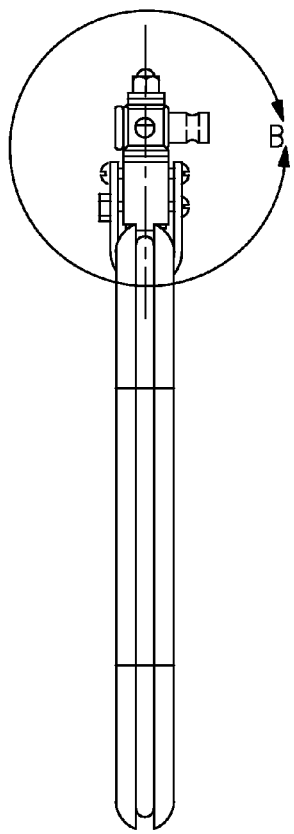
FIG. 6 illustrates a right side view of the LTPS of FIG. 1.
Figure 11:
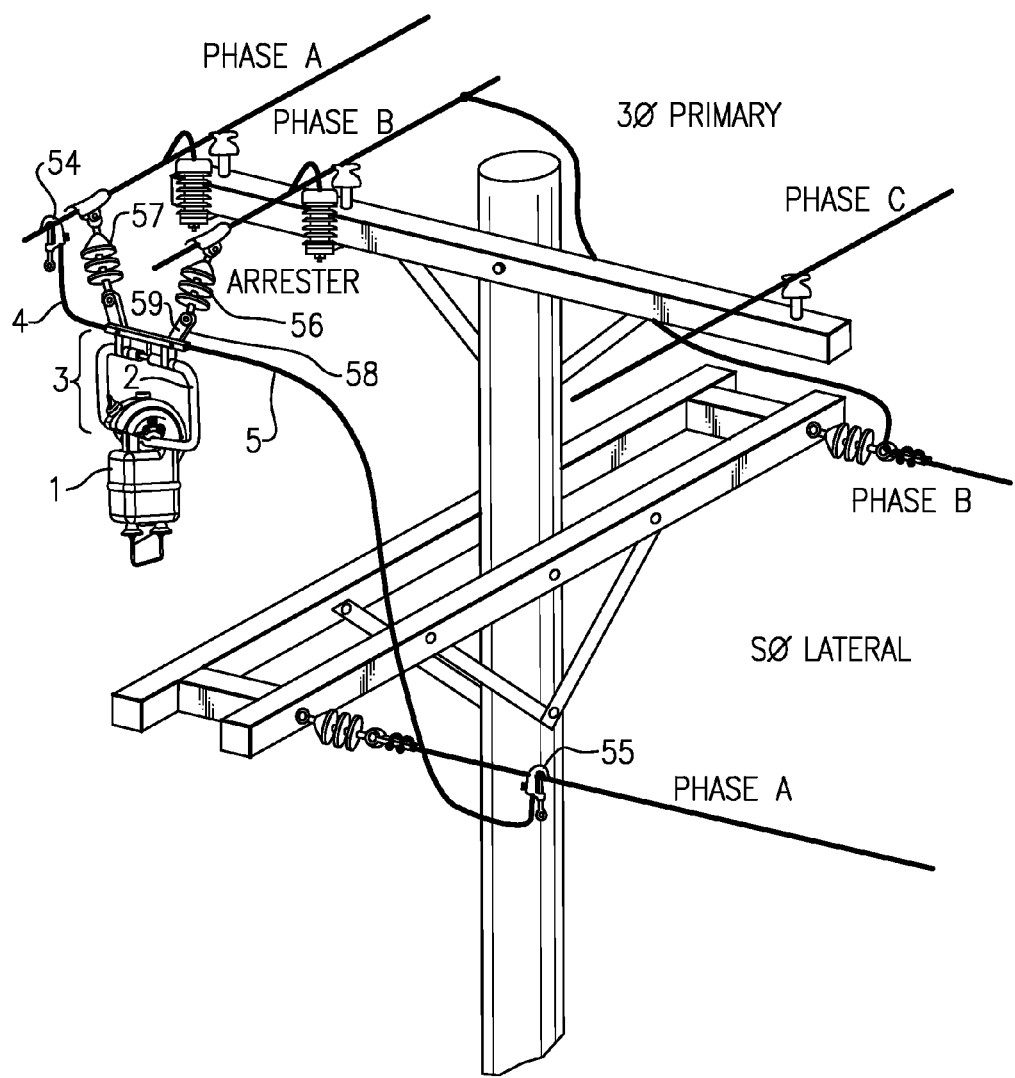
FIG. 11 illustrates the LTPS suspended from phase A and phase B conductors with suspension insulators for measuring current in phase A for the delta connected electric power system.

FIG. 11 illustrates a second method of installation using two suspension insulators 56 and 57 mounted on phase A and phase B of the delta connected system. Links 58 and 59 are attached to the suspension insulators 56 and 57 on one end, and the pins 40 (shown in FIGS. 6 and 7) are inserted through bottom end holes of the links 58 and 59 and through the left and right anchor rods 11, and 31. Cotter pins are installed in holes 40a (see FIGS. 5 and 7) in the pins 40 to hold the left and right anchor rods 11 and 31 to the links 58 and 59. With the original jumper J1 of FIG. 9 in place, insuring no interruption of service, the power line conductor 4 is attached to phase A of the 3∅primary using a hotstick and the hot line clamp 54. Similarly, the power line conductor 5 is attached to phase A of the S∅ lateral using the hotstick and the hotline clamp 55, the original jumper J1 of FIG. 9 is then removed, and current now flows from phase A of the 3∅ primary to the phase A of the S∅ lateral through the winding of wire 6 of the LTPS 3. The STR unit 1 is then installed on the loop tube 2 of the LTPS 3 and as before transmits data.

Figure 12:
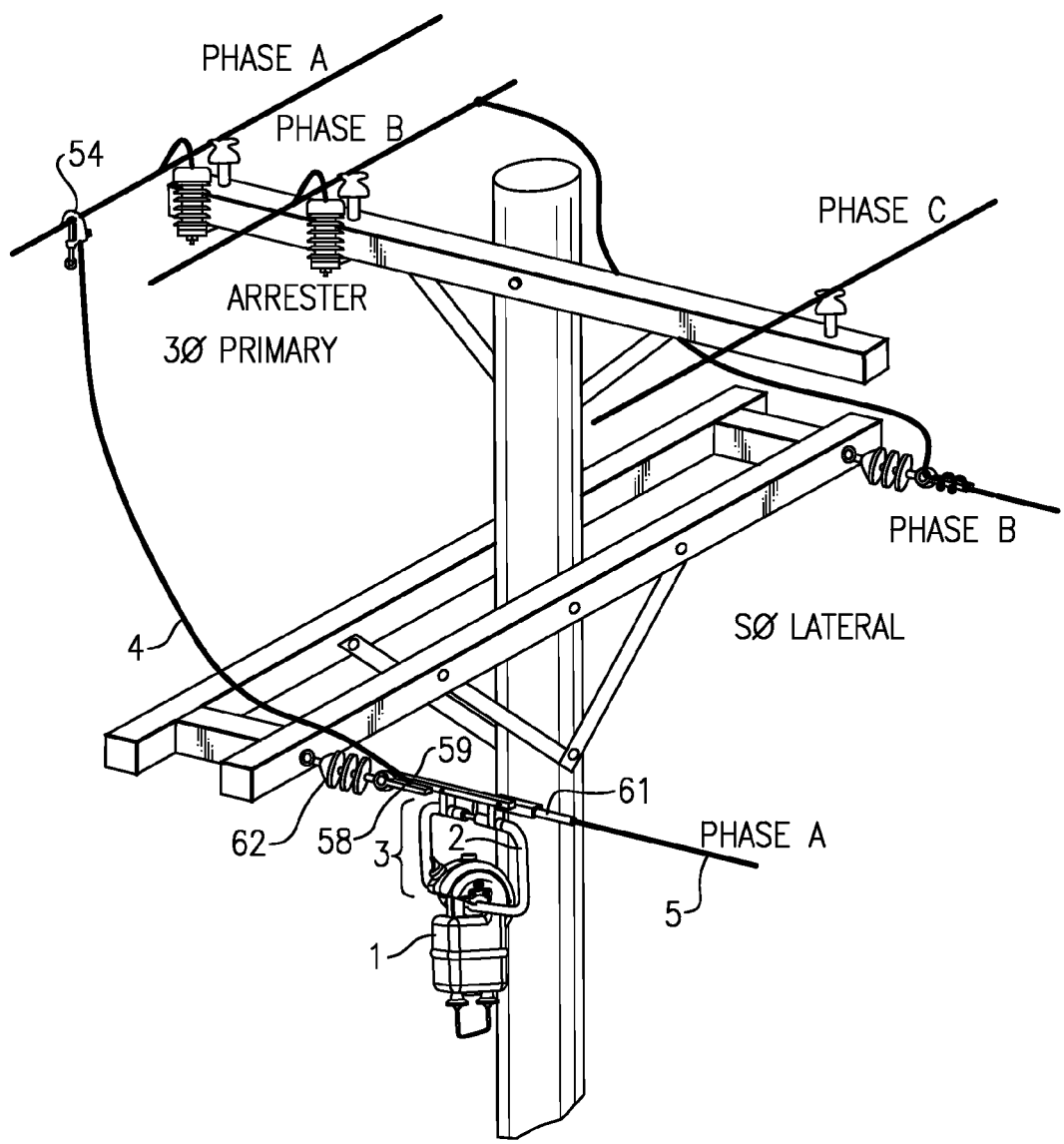
FIG. 12 illustrates a single dead ended LTPS installed on phase A for measuring current in phase A for the delta connected electric power system.

FIG. 12 illustrates a third method of installation using an automatic dead end 61 shown in FIG. 1 on the right side of the loop tube 2 and the links 58 and 59 of FIG. 11 on the left side for the delta connected system. The automatic dead end 61 is a commercially available product which allows the power line conductor 5 to be inserted into spring loaded jaws internal to the device upon which applying tension to the power line conductor 5 automatically grips the power line conductor.

The left end of the automatic dead end 61 is formed into a "U" bracket with a hole in the end which fits onto the right side anchor rod 31 using pin 40 and cotter pin. The end of the power line conductor 5 is then inserted into the hole in the end of the right side anchor rod 31 and held electrically in contact with same using the two set screws 12 of FIG. 8. The left side anchor rod 11 is attached to the two links 58 and 59 using pin 40 and cotter pin, and the left ends of the links 58 and 59 are attached to a dead end insulator 62 using pin 40 and cotter pin. Here again the original jumper J1 of FIG. 9 remains in place while the LTPS 3 is being installed. As before, the power line conductor 4 is tapped to phase A of the 3∅primary using hot line clamp 54, the original jumper J1 is removed, and then the STR unit 1 is installed using a hot stick on the loop tube 2.

Figure 13:
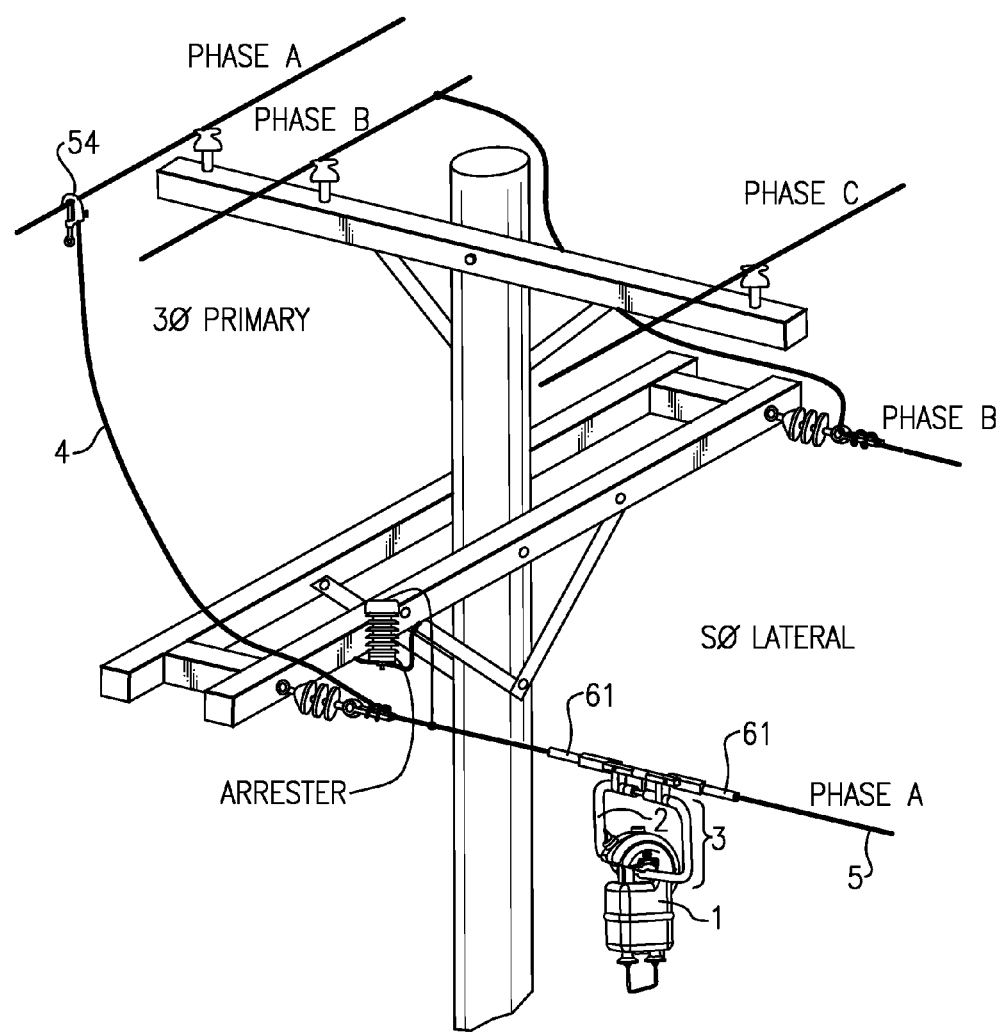
FIG. 13 illustrates a double dead ended LTPS installed on phase A for measuring current in phase A for the delta connected electric power system.

FIG. 13 illustrates a fourth method of installation similar to the method shown in FIG. 12, except two automatic dead ends 61 are used as in FIG. 1. The same process of installing the automatic dead end 61 of the third method shown in FIG. 12 is applied to both the left side anchor rod 11 and the right side anchor rod 31. Again the original jumper J1 as shown in FIG. 9 remains connected until the hot line clamp 54 and power line conductor 4 are installed.

Figure 14:
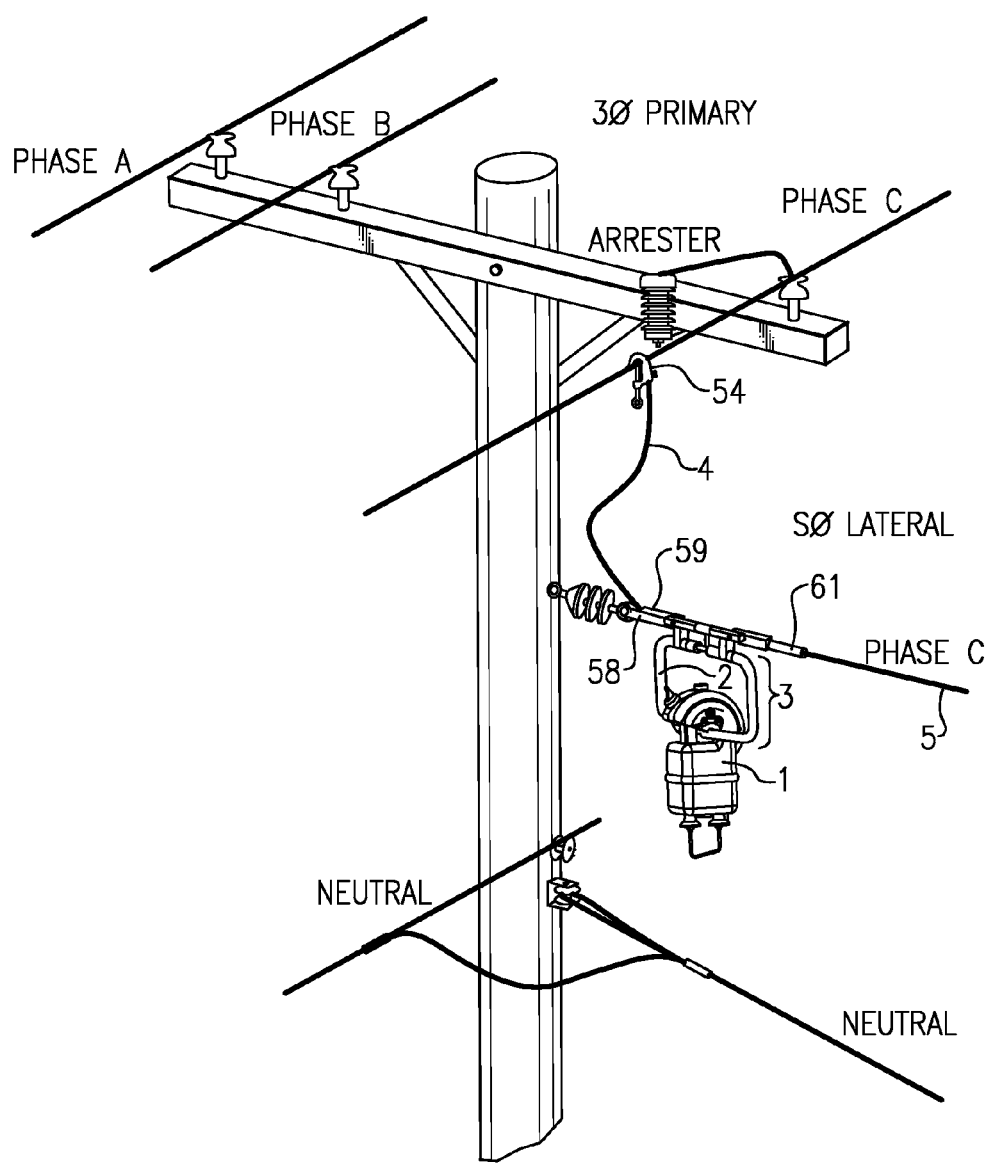
FIG. 14 illustrates a single dead ended LTPS installed on phase C for measuring current in phase C for wye connected electric power system.

FIG. 14 illustrates a fifth method of installation similar to the method shown in FIG. 12 except applied to a wye connected electric power system with the phase C current being measured on the S∅ lateral.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A device connectable to an electric power line conductor comprising:
    an electrically conductive insulated wire wound at least twice around a loop tube having a first end and a second end, wherein the wire is configured to be connected in series with a power line conductor; and
    a housing including a pair of jaws mountable to the loop tube including an iron core power supply transformer configured to surround the wire to power a power supply module.

2. The device of claim 1 wherein the loop tube is a hollow loop with a slot around a periphery, wherein the slot is configured to accept the wire.

3. The device of claim 2 wherein the slot forms a heat transfer fin configured to remove heat from wire.

4. The device of claim 1 wherein the wire passes through the iron core power supply at least as many times as the wire is wound.

5. The device of claim 1 wherein the wire is configured to multiply the current realized by the power supply transformer to provide higher secondary voltage and higher secondary current to power the device.

6. The device of claim 2 wherein the wire is configured to be mechanically attached to the power line conductor.

7. The device of claim 1 wherein the wire is wound at least three times.

8. The device of claim 1 including an electrically insulated bridge mounted between the first end of the wire and the second end of the wire to prevent forces on the wire created by excessive power line fault current from pushing the wires apart.

9. The device of claim 2 including a first anchor rod electrically isolated from a second anchor rod.

10. The device of claim 9 wherein the first anchor rod is configured to attach to the power line conductor and a anchor rod is configured to attach to the power line conductor and a shorting bar electrically connecting the first anchor rod and the second anchor rod for electrically bypassing the wire.

11. The device of claim 9 including an electrically insulating spacer rod located between a first anchor rod and a second anchor rod, the spacer rod supports the wire and the housing and is configured to provide an electrically conductive path between the power line conductor and for providing tension in the power line conductor.

12. The device of claim 9 including at least one of an automatic dead end or a link attached to a first hole in the first anchor rod and secured with a retention pin.

13. The device of claim 12 including at least one of an automatic dead end or a link attached to a first hole in the second anchor rod and secured with a retention pin.

14. The device of claim 9 including a first hole in the first anchor rod and a second hole in the second anchor rod, wherein the first hole is configured to accept a first end cap on a first insulated post and the second hole is configured to accept a second end cap on a second insulated post.

15. The device of claim 9 including a first hole in the first anchor rod and a second hole in the second anchor rod, wherein the first hole is configured to accept a first link attached to a first suspension insulator and the second hole is configured to accept a second link attached to a second suspension insulator.

16. A device connectable to an electric power line conductor comprising:
a loop tube providing a form;
at least two turns of electrically conductive and insulated wire surrounding the loop tube configured to be connected in series with an electric power line conductor;
a housing mountable to the wire including an iron core power supply transformer configured to surround the wire to power a power supply module; and
a shorting bar for electrically bypassing the wire.

17. The device of claim 16 including a slot on a periphery of the loop tube for accepting the wire.

18. A device connectable to an electric power line conductor comprising:
a loop tube providing a form including a slot for accepting a first locking device, the first locking device including a projection on one end that has a width approximately equal to a slot width and a depth approximately equal to a wall thickness of the loop tube;
at least two turns of electrically conductive and insulated wire surrounding the loop tube configured to be connected in series with a electric power line conductor; and
a "U" shaped first band for holding the projection into the slot and preventing the loop tube from rotating with respect to the wire located within the loop tube.

19. The device of claim 18 including a first band having a first end adjacent the projection holding the loop tube to the first locking device and a second end affixed to the other end of the first locking device.

20. The device of claim 19 wherein the loop tube, the first locking device, and the first band are affixed to a member, the member is configured to be connected to the first power line conductor.

21. The device of claim 20 including a second locking device spaced from the first locking device and a second band spaced from the first band for supporting the loop tube and the wire.

22. The device of claim 21 wherein the first locking device is attached to a first member and the first member is configured to be attached to the power line conductor and the second locking device is attached to a second member and the second member is configured to be attached to the power line conductor.

23. The device of claim 22 including a first connector attached to a first end of the wire and a second connector attached to a second end of the wire.

24. The device of claim 16 including a bracket configured to be mounted to a pole having at least one cantilevered insulator engaging the device and configured to be attached to a pole.

25. The device of claim 24 wherein the at least one cantilevered insulator engages a hole in an anchor rod.

26. The device of claim 1 including a shorting bar for electrically bypassing the wire.

* * * * *